US006514434B1

(12) United States Patent
He et al.

(10) Patent No.: US 6,514,434 B1
(45) Date of Patent: Feb. 4, 2003

(54) ELECTRO-OPTIC CHROMOPHORE BRIDGE COMPOUNDS AND DONOR-BRIDGE COMPOUNDS FOR POLYMERIC THIN FILM WAVEGUIDES

(75) Inventors: Mingqian He, Painted Post, NY (US); Thomas M. Leslie, Horseheads, NY (US)

(73) Assignee: Corning Incorporated, Corning, NY (US)

( * ) Notice: Subject to any disclaimer, the term of this patent is extended or adjusted under 35 U.S.C. 154(b) by 122 days.

(21) Appl. No.: 09/595,980

(22) Filed: Jun. 16, 2000

(51) Int. Cl.[7] ................................................. F21V 8/00
(52) U.S. Cl. ........................... 252/582; 549/505; 549/1; 508/18; 508/11; 508/38; 359/321; 252/586
(58) Field of Search ................................ 252/582, 586; 549/505, 1; 568/18, 11, 38; 359/321

(56) References Cited

U.S. PATENT DOCUMENTS

| | | | |
|---|---|---|---|
| 4,014,951 A | | 3/1977 | Naf et al. |
| 4,767,169 A | | 8/1988 | Teng et al. |
| 4,795,654 A | | 1/1989 | DeMartino |
| 4,810,338 A | | 3/1989 | DeMartino et al. |
| 4,936,645 A | | 6/1990 | Yoon et al. |
| 5,006,285 A | | 4/1991 | Thaekara et al. |
| 5,044,725 A | | 9/1991 | DeMartino et al. |
| 5,106,211 A | | 4/1992 | Chiang et al. |
| 5,133,037 A | | 7/1992 | Yoon et al. |
| 5,156,774 A | * | 10/1992 | Leising et al. |
| 5,170,461 A | | 12/1992 | Yoon et al. |
| 5,187,234 A | | 2/1993 | Leslie et al. |
| 5,196,509 A | | 3/1993 | Allen |
| 5,247,042 A | | 9/1993 | Allen et al. |
| 5,290,630 A | | 3/1994 | Devonald et al. |
| 5,320,936 A | * | 6/1994 | Kumagai et al. |
| 5,326,661 A | | 7/1994 | Sansone et al. |
| 6,057,316 A | | 5/2000 | Wrobel et al. |
| 6,067,186 A | | 5/2000 | Dalton et al. ............... 359/321 |
| 6,114,031 A | | 9/2000 | Roberts et al. |
| 6,348,992 B1 | * | 2/2002 | Zhang et al. |

FOREIGN PATENT DOCUMENTS

JP 3-101671 A 4/1991
WO WO 98/56749 12/1998

OTHER PUBLICATIONS

U.S. patent application Ser. No. 09/596,069, He et al., filed Jun. 16, 2000.
U.S. patent application Ser. No. 09/675,966, He et al., filed Sep. 29, 2000.
U.S. patent application Ser. No. 09/595,221, He et al., filed Jun. 16, 2000.
U.S. patent application Ser. No. 09/675,967, He et al., filed Sep. 29, 2000.
Reddy et al., "Vilsmeier Reaction on Some 6 & 7–Methoxy–1–tetralols," *Indian Journal of Chemistry*, 20B:100–103 (1981).
Wang et al., "Design, Synthesis and Characterization of a Novel Substituted Dicyanomethylendihydrofuran Based High–B NLO Chromophore and Its Polymers with Exceptionally High Electro–Optic Coefficients," *Polymer Preprints*, 39(2):1065–1066 (1998).
Zhang et al., "A Novel Trilinkable High $\mu$B NLO Chromophore for Polymeric Electro–optic Material With Enhanced Thermal Stability," *Polymer Preprints*, 40:156–157 (1999).
Ren et al., "A Trifunctionalized High $\mu$B Chromophore and Its 3D Polyurethane Network With Enhanced NLO Alignment Stability for Electro–optic Device Applications," *Polymer Preprints*, 40:160–161 (1999).
Ren, "Electro Active Polymer Thin Films for Fabrication of Ultra–high Bandwidth Integrated Electro–optic Modulators," Ph.D. Thesis, University of Southern California (1999).
Todorova et al., "New NLO Cromophores Based on 2–amino–1,1,3–tricyano–1–propene Acceptor," *Polymeric Materials: Science and Engineering*, 83:256–257 (2000).

* cited by examiner

Primary Examiner—Margaret G. Moore
Assistant Examiner—Kuo-Liang Peng
(74) Attorney, Agent, or Firm—Walter M. Douglas; Peter Rogalskyj

(57) ABSTRACT

The present invention is directed to electro-optico chromophore bridge compounds and donor-bridge compounds which can be used in the preparation of polymeric thin films for waveguide media.

24 Claims, No Drawings

ELECTRO-OPTIC CHROMOPHORE BRIDGE COMPOUNDS AND DONOR-BRIDGE COMPOUNDS FOR POLYMERIC THIN FILM WAVEGUIDES

FIELD OF THE INVENTION

The present invention relates generally to electro-optic chromophore bridge compounds and donor-bridge compounds which can be used in the preparation of chromophores for use in polymeric thin films for waveguide media, and specifically to organic nonlinear chromophore bridge compounds and donor-bridge compounds for polymeric switches and modulators.

BACKGROUND OF THE INVENTION

Thin films of organic or polymeric materials with large second order nonlinearities in combination with silicon-based electronic circuitry can be used in systems for laser modulation and deflection, information control in optical circuitry, as well as in numerous other waveguide applications. In addition, novel processes through third order nonlinearity such as degenerate four-wave mixing, whereby real-time processing of optical fields occurs, have utility in such diverse fields as optical communications and integrated circuit fabrication. The utility of organic materials with large second order and third order nonlinearities for very high frequency applications contrasts with the bandwidth limitations of conventional inorganic electro-optic materials currently in use.

Numerous optically responsive monomers and polymers have been developed for use in organic materials which, in turn, can be used in the waveguide applications described above. For example, U.S. Pat. No. 5,044,725, which is incorporated herein by reference in its entirety, describes numerous polymer compositions which provide suitable nonlinear optical response. U.S. Pat. No. 5,044,725 describes, for example, a preferred polymer composition comprising an organic structure containing an electron donating group and an electron withdrawing group at opposing termini of a bridge.

Synthesis of high performance organic, high $\mu\beta$ electro-optic chromophores must be accomplished in order to make polymer-based electro-optic devices. The synthesis of electro-optic chromophore bridge compounds and donor-bridge compounds for organic nonlinear optical applications is generally known in the art. Although some bridge compounds and donor-bridge compounds have been reported in the literature, many of them have showed several and sometimes severe problems ranging from thermal instability, insolubility in the polymer, photodegradability, exhibition of a broad absorption band into the wavelength region of interest, and large birefringence upon poling. Accordingly, suitable electro-optic chromophore bridge compounds and donor-bridge compounds are desired.

SUMMARY OF THE INVENTION

The present invention is directed to compounds which can serve as electro-optic chromophore bridge compounds for use in, for example, thin polymer films for waveguides. Preferred bridge compounds of the invention have Formula I.

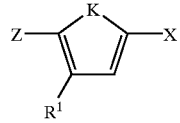

Preferably, K is O or S. Preferably, $R^1$ is —Q—$C_nH_{2n+1}$, —Q—$(CH_2)_aC_nF_{2n+1}$, —Q—$CH_2SCH_2C_nF_{2+1}$, or —Q—$CH_2SCH_2CF_3$, where n is 1–10 and a is 0–10, or —Q—$CH_2OCH_2CF_3$. Other halogens or deuterium can be used in place of F. Q preferably is either absent or, when present, O or S. X preferably has the formula H or —(CH═CH)$_b$C(═O)H, where b is 0–3. Z is a chemical group that is capable of being linked to a donor and includes, but is not limited to, Br, I, —$CH_2$—Br, —$CH_2$—OH, —$CH_3$, —C(═O)H, —(CH═$CH_2$)$_n$ where n is 1–3, and the like. Those skilled in the art can use additional groups known to those skilled in the art to couple a bridge compound to a donor. Another Z group that can used to link a bridge compound to a donor is

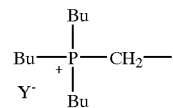

where $Y^-$ is a counter ion.

Other preferred bridge compounds of the invention have Formula II.

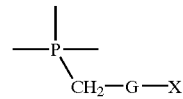

G is preferably —C≡C—C≡C—. X preferably is H or ═CH(—CH═CH)$_d$—C(═O)H, where d is 0–3.

Other preferred bridge compounds of the invention have Formula III.

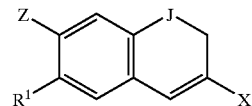

Preferably, J is $CH_2$, O or S. Preferably, $R^1$ is —Q—$C_nH_{2n+1}$, —Q—$(CH_2)_aC_nF_{2n+1}$, —Q—$CH_2SCH_2C_nF_{2n+1}$, or —Q—$CH_2SCH_2CF_3$, where n is 1–10 and a is 0–10, or —Q—$CH_2OCH_2CF_3$. Other halogens or deuterium can be used in place of F. Q preferably is either absent or, when present, O or S. X preferably has the formula (C═O)H, or C═CH(—CH═CH)$_d$—C(═O)H, where d is 0–3. Z is a chemical group that is capable of being linked to a donor and includes, but is not limited to, —$CH_2$—Br, —$CH_2$—OH, —$CH_3$, —C(═O)H, Br, I, and the like. Those skilled in the art can use additional groups known to those skilled in the art to couple a bridge compound to a donor. Another Z group that can be used to link a bridge compound to a donor is

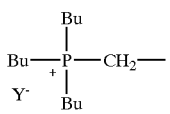

where $Y^-$ is a counter ion.

The present invention is also directed to compounds which can serve as electro-optic chromophore donor-bridge compounds for use in, for example, thin polymer films for waveguides.

Preferred donor-bridge compounds of the invention have Formula IV.

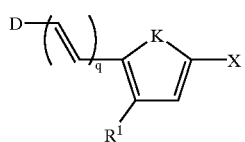

IV

Preferably, K is O or S. D is preferably an electron donating group. Preferably, $R^1$ is $-Q-C_nH_{2n+1}$, $-Q-(CH_2)_aC_nF_{2n+1}$, $-Q-CH_2SCH_2C_nF_{2n+1}$, or $-Q-CH_2SCH_2CF_3$, where n is 1–10 and a is 0–10, or $-Q-CH_2OCH_2CF_3$. Other halogens or deuterium can be used in place of F. Q preferably is either absent or, when present, O or S. X preferably has the formula H or $(-CH=CH)_b-C(=O)H$, where b is 0–3. Preferably, q is 1, 2, or 3.

Other preferred donor-bridge compounds of the invention have Formula V.

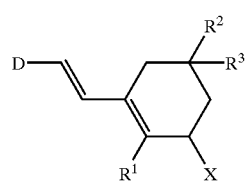

V

Preferably, $R^1$ is H, $-Q-CH_{2n+1}$, $-Q-(CH_2)_aC_nF_{2n+1}$, $-Q-CH_2SCH_2C_nF_{2n+1}$, or $-Q-CH_2SCH_2CF_3$, where n is 1–10 and a is 0–10, or $-Q-CH_2OCH_2CF_3$. Other halogens or deuterium can be used in place of F. Q preferably is either absent or, when present, O or S. D is preferably an electron donating group. X preferably has the formula (=O), or $=CH(-CH=CH)_d-C(=O)H$, where d is 0–3. $R^2$ and $R^3$ each, independently, are preferably $C_nH_{2n+1}$ where n is 2–10.

Other preferred donor-bridge compounds of the invention have Formula VI.

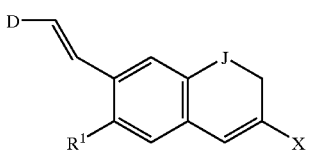

VI

Preferably, J is $CH_2$, O or S. Preferably, $R^1$ is $-Q-C_nH_{2n+1}$, $-Q-(CH_2)_aC_nF_{2n+1}$, $-Q-CH_2SCH_2C_nF_{2n+1}$, or $-Q-CH_2SCH_2CF_3$, where n is 1–10 and a is 0–10, or $-Q-CH_2OCH_2CF_3$. Other halogens or deuterium can be used in place of F. Q preferably is either absent or, when present, O or S. D is preferably an electron donating group. X preferably has the formula (C=O)H, or $C=CH(-CH=CH)_d-C(=O)H$, where d is 0–3.

DESCRIPTION OF PREFERRED EMBODIMENTS OF THE INVENTION

The present invention relates, in part, to novel electro-optic chromophore bridge compounds and donor-bridge compounds which have utility in organic nonlinear optical applications. Electro-optic chromophores comprising the donor-bridge compounds of the invention exhibit thermal stability to temperatures from 260° C. to 310° C. Chromophores comprising the donor-bridge compounds of the invention also show great solubility in most common organic solvents and, thus, are useful in most polymer films for waveguides. In addition, under intense UV-irradiation (365 nm, dosage 3 J/cm$^2$ up to 13 minutes), the chromophores comprising the donor-bridge compounds of the invention show no changes of UV-VIS-NIR spectrum, which indicates that the chromophores are, to a major extent, photo stable.

The compounds of the invention can be used in, for example, polymeric organic materials for optical waveguides. Such polymeric organic materials are described in, for example, U.S. Pat. Nos. 5,044,725, 4,795,664, 5,247,042, 5,196,509, 4,810,338, 4,936,645, 4,767,169, 5,326,661, 5,187,234, 5,170,461, 5,133,037, 5,106,211, and 5,006,285, each of which is incorporated herein by reference in its entirety.

The phrase "electron donating group" is used synonymously with "electron donator" and refers to substituents which contribute electron density to the π-electron system when the conjugated electron structure is polarized by the input of electromagnetic energy.

The phrase "donor-bridge compound" refers to an electron donating group coupled to a bridge compound of the invention.

In preferred embodiments of the invention, the electro-optic chromophore bridge compounds comprise Formula I:

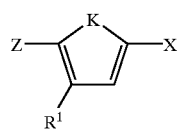

I

Preferably, K is O or S.

Preferably, $R^1$ is $-Q-C_nH_{2n+1}$, $-Q-(CH_2)_aC_nF_{2n+1}$, $-Q-CH_2SCH_2C_nF_{2n+1}$, or $-Q-CH_2SCH_2CF_3$, where n is 1–10 and a is 0–10, or $-Q-CH_2OCH_2CF_3$. Other halogens or deuterium can be used in place of F. Q preferably is either absent or, when present, O or S. By modification of the substituents on the bridge compound, fluorinated or deuterated alkyl groups can replace the hydrocarbon substituents and can make the chromophore compounds comprising the bridge compounds more compatible with highly halogenated low loss polymers.

In more preferred embodiments of the invention, a is 1–3 and n is 1–10. In more preferred embodiments of the invention, $R^1$ is $C_1-C_{10}$, more preferably $C_4-C_{10}$, and may contain fluorine substitutions.

X preferably has the formula H or $-(CH=CH)_b-C(=O)H$, where b is 0–3. Most preferably, b is 0–2. The terminal aldehyde group serves as the preferred site of reaction with electron withdrawing groups. In more preferred embodiments of the invention, b is 0 so that X is $-C(=O)H$.

Z is a chemical group that is capable of being linked to the donor and includes, but is not limited to, Br, I, —CH$_2$—Br, —CH$_2$—OH, —CH$_3$, —C(=O)H, —(CH=CH$_2$)$_n$ where n is 1—3, and the like. Those skilled in the art can use additional groups known to those skilled in the art to couple a bridge compound to a donor. Another Z group that can be used to the link a bridge compound to a donor is:

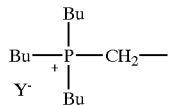

where Y$^-$ is a counter ion including, but not limited to, Br$^-$, I$^-$, or Cr$^-$.

In addition, the thiophene ring can also be substituted at the open position (3') with, for example, an R$^1$ moiety as described above. Further, the Bu groups can be substituted by, for example, phenyl groups.

In other preferred embodiments of the invention, the electro-optic chromophore bridge compounds comprise Formula II:

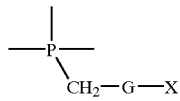

II

G is preferably —C≡C—C≡C—. X preferably is H or =CH(—CH=CH)$_d$—C(=O)H, where d is 0–3. In more preferred embodiments of the invention, X is (=O).

In other preferred embodiments of the invention, the electro-optic chromophore bridge compounds comprise Formula III:

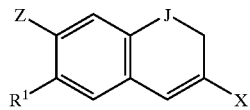

III

Preferably, J is CH$_2$, O or S.

Preferably, R$^1$ is —Q—C$_n$H$_{2n+1}$, —Q—(CH$_2$)$_a$C$_n$F$_{2n+1}$, —Q—CH$_2$SCH$_2$C$_n$F$_{2n+1}$, or —Q—CH$_2$SCH$_2$CF$_3$, where n is 1–10 and a is 0–10, or —Q—CH$_2$OCH$_2$CF$_3$. Other halogens or deuterium can be used in place of F. Q preferably is either absent or, when present, C or S. In more preferred embodiments of the invention, a is 1–3 and n is 1–3. In more preferred embodiments of the invention, R is C$_1$–C$_{10}$, more preferably C$_4$–C$_{10}$, and may contain fluorine substitutions.

X preferably has the formula (C=O)H, or C=CH(—CH=CH)$_d$—C(=O)H, where d is 0–3. In more preferred embodiments of the invention, X is C(=O)H.

Z is a chemical group that is capable of being linked to a donor and includes, but is not limited to, Br, I, —CH$_2$—Br, —CH$_2$—OH, —CH$_3$, —C(=O)H, —(CH=CH$_2$)$_n$ where n is 1—3, and the like. Those skilled in the art can use additional groups known to those skilled in the art to couple a bridge compound to a donor. Another Z group that can be used to link a bridge compound to a donor is:

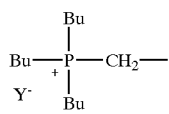

where Y$^-$ is a counter ion including, but not limited to, Br$^-$, I$^-$, or Cl$^-$.

In other embodiments of the invention, the electro-optic chromophore bridge compound is coupled to an electron donating group to form an electro-optic chromophore donor bridge compound. In some preferred embodiments of the invention, the donor-bridge compounds comprise Formula IV.

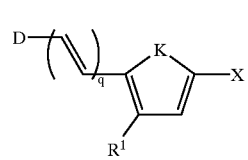

IV

In Formula IV, a bridge compound having Formula I is coupled to an electron donating group D. Preferred electron donating groups include, but are not limited to, a phenyl ring substituted in the para position by, for example, amino, alkylamino, dialkylamino, 1-piperidino, 1-piperazino, 1-pyrrolidino, acylamino, hydroxyl, thiolo, alkylthio, arylthio, alkoxy, aryloxy, acyloxy, 1,2,3,4-tetrahydroquinolinyl, and the like.

Preferably, K is O or S.

Preferably, R$^1$ is —Q—C$_n$H$_{2n+1}$, —Q—(CH$_2$)$_a$C$_n$F$_{2n+1}$, —Q—CH$_2$SCH$_2$C$_n$F$_{2n+1}$, or —Q—CH$_2$SCH$_2$CF$_3$, where n is 1–10 and a is 0–10, or —Q—CH$_2$OCH$_2$CF$_3$. Other halogens or deuterium can be used in place of F. Q preferably is either absent or, when present, O or S. By modification of the substituents on the bridge compound, fluorinated or deuterated alkyl groups can replace the hydrocarbon substituents and can make the chromophore compounds comprising the bridge compounds more compatible with highly halogenated low loss polymers. In more preferred embodiments of the invention, a is 1–3 and n is 1–10. In more preferred embodiments of the invention, R$^1$ is C$_1$–C$_{10}$, more preferably C$_4$–C$_{10}$, and may contain fluorine substitutions.

X preferably has the formula H or —(CH=CH)$_b$—C(=O)H, where b is 0–3. Most preferably, b is 0–2. The terminal aldehyde group serves as the preferred site of reaction with electron withdrawing groups. In more preferred embodiments of the invention, b is 0 so that X is —C(=O)H.

Most preferably, electron donating group D couples with a bridge compound having Formula I to produce a donor-bridge compound having Formula VII.

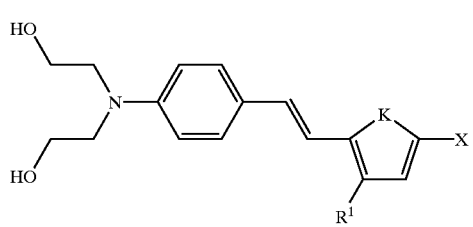

VII

In other preferred embodiments of the invention, the donor-bridge compounds comprise Formula V.

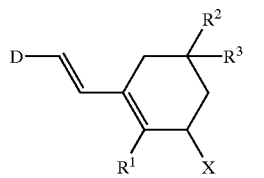

V

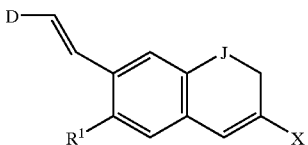

VI

In Formula VI, a bridge compound having the depicted formula is coupled to an electron donating group D. Preferred electron donating groups include, but are not limited to, a phenyl ring substituted in the para position by, for example, amino, alkylamino, dialkylamino, 1-piperidino, 1-piperazino, 1-pyrrolidino, acylamino, hydroxyl, thiolo, alkylthio, arylthio, alkoxy, aryloxy, acyloxy, 1,2,3,4-tetrahydroquinolinyl, and the like.

Preferably, $R^1$ is H, $-Q-C_nH_{2n+1}$, $-Q-(CH_2)_aC_nF_{2n+1}$, $-Q-CH_2SCH_2C_nF_{2n+1}$, or $-Q-CH_2SCH_2CF_3$, where n is 1–10 and a is 0–10, or $-Q-CH_2OCH_2CF_3$. Other halogens or deuterium can be used in place of F. Q preferably is either absent or, when present, O or S.

X preferably has the formula (=O), or =CH(—CH=CH)$_d$—C(=O)H, where d is 0–3. $R^2$ and $R^3$ each, independently, are preferably $C_1$, $C_2$ or $C_3$ alkyl.

Most preferably, electron donating group D couples with a bridge compound to produce a donor-bridge compound having Formula VIII.

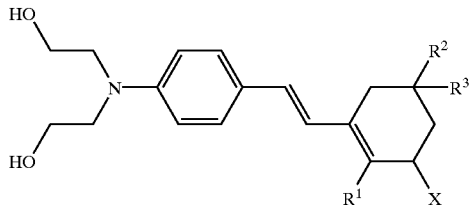

VIII

In other preferred embodiments of the invention, the donor-bridge compounds comprise Formula VI.

In Formula VI, a bridge compound having Formula III is coupled to an electron donating group D. Preferred electron donating groups include, but are not limited to, a phenyl ring substituted at the para position by, for example, amino, alkylamino, dialkylamino, 1-piperidino, 1-piperazino, 1-pyrrolidino, acylamino, hydroxyl, thiolo, alkylthio, arylthio, alkoxy, aryloxy, acyloxy, 1,2,3,4-tetrahydroquinolinyl, and the like.

Preferably, J is $CH_2$, O or S.

Preferably, $R^1$ is $-Q-C_nH_{2n+1}$, $-Q-(CH_2)_aC_nF_{2n+1}$, $-Q-CH_2SCH_2C_nF_{2n+1}$, or $-Q-CH_2SCH_2CF_3$, where n is 1–10 and a is 0–10, or $-Q-CH_2OCH_2CF_3$. Other halogens or deuterium can be used in place of F. Q preferably is either absent or, when present, O or S.

X preferably has the formula (C=O)H, or C=CH(—CH=CH)$_d$—C(=O)H, where d is 0–3.

Most preferably, electron donating group D couples with a bridge compound having Formula III to produce a donor-bridge compound having Formula IX.

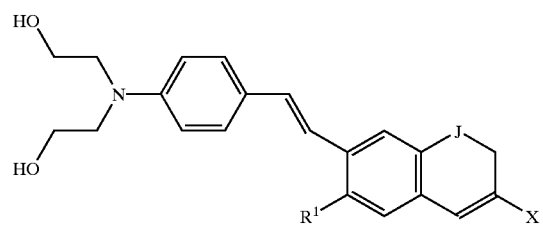

IX

The invention is further illustrated by way of the following examples which are intended to elucidate the invention. These examples are not intended, nor are they to be construed, as limiting the scope of the disclosure.

EXAMPLES

Example 1

Preparation of a Compound Having Formula I

Compounds having Formula I have been synthesized as described below.

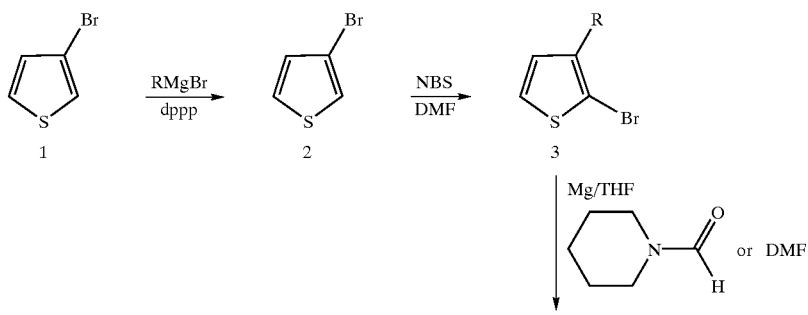

-continued

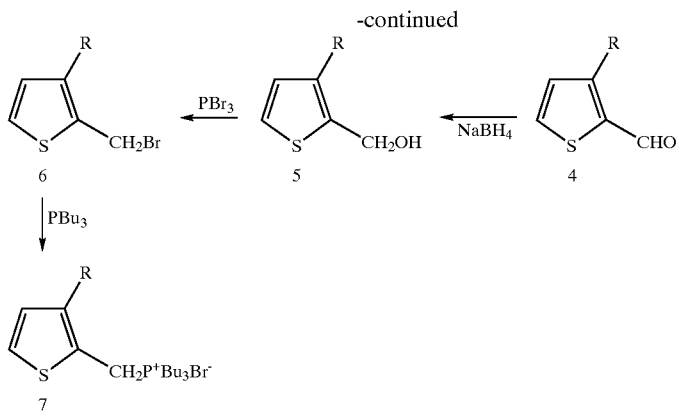

Briefly, 3bromothiophene (81.5 g, 0.5 mol) was dissolved into 300 ml dry ethyl ether. [1,3-Bis(diphenylphosphino)propane]dichloronickel(ii) (dppp) was added in a catalytic amount. To this mixture in an ice bath, decylmagnesium bromide (600 ml, 0.6 mol, 1 M in ethyl ether) was added slowly. After the addition, the mixture was warmed up and refluxed for 48 hours. After cooling in an ice bath, 5% HCl solution was added slowly. The organic layer was separated, washed with saturated $NaHCO_3$ (100 ml), brine (100 ml), and water (2×50 ml). The organic solution was dried over $MgSO_4$. The solvent was evaporated, followed by vacuum distillation (101° C./0.3 mm Hg) to give pure compond 2 where R is $C_{10}H_{21}$ (85 g, 75.9%).

Compound 2 (23 g, 0.103 mol) was mixed with dry DMF. To this mixture N-bromosuccinimide (18.3 g, 0.103 mol) in DMF (50 ml) was added in the dark at 0° C. The mixture was stirred at room temperature overnight, poured into 500 ml of water, and extracted with ethyl ether (3×100 ml). The combined organic solution was washed with brine (100 ml), water (2×50 ml), and dried over anhydrous $MgSO_4$. After evaporating the solvent, compound 3 was collected by vacuum distillation (105° C./0.12 mm Hg) to give 31.1 g (96.8%) yield.

Magnesium chips (4.8 g, 0.2 mol) and dry THF (100 ml) were placed in a 500 ml three-neck flask. Compound 3 (74 g, 0.194 mol) was poured in. The mixture was stirred and observed carefully to avoid overheating by cooling in an ice bath as needed. The solution was kept refluxing until almost all the magnesium metal disappeared. The solution was then transferred to another flask and 1-formylpiperidine (33.9 g, 0.3 mol) was added dropwise. The final solution was refluxed 24 hours and cooled to room temperature. After the mixture was cool, 3 M HCl (100 ml) was added and the mixture stirred at room temperature. After an hour, most of the THF was evaporated. The remaining mixture was extracted using ether (3×100 ml). The combined organic solution was washed with saturated $NaHCO_3$ (50 ml), brine (100 ml), water (2×50 ml) and dried over anhydrous $MgSO_4$. The crude product was purified through column chromatography on silica using 5% ethyl acetate to give Compound 4 (27.3 g, 42.6% yield).

Compound 4 (27.3 g, 0.082 mol) was dissolved into MeOH (300 ml). To this solution, $NaBH_4$ (1.56 g, 0.041 mol) and NaOH (1 ml, 50% water solution) in 30 ml MeOH was added dropwise in an ice bath. The resulting solution was stirred 8 hours at room temperature. After evaporating most of the MeOH, the rest of the mixture was extracted with ethyl ether (3×100 ml). The combined organic mixture was washed with 1 M HCl (30 ml), saturated $NaHCO_3$ (50 ml), brine (100 ml), water (50 ml) and dried over anhydrous $MgSO_4$. After evaporating the ether, Compound 5 was left and checked using HNMR and found to be pure enough for the next step. The conversion ratio was 100%.

Compound 5 (21.2 g, 0.064 mol) was dissolved into 100 ml of ethyl ether. To this mixture, $PBr_3$ (8.6 g, 0.032 mol) was added dropwise. The mixture was stirred for 8 hours and then poured into saturated $NaHCO_3$ solution. The organic material was extracted using ethyl ether (3×80 ml). The combined organic mixture was washed with brine (100 ml), water (2×100 ml) and dried over anhydrous $MgSO_4$. After evaporating the solvent, the Compound 6 was checked using HNMR and found to be pure enough for the next reaction.

Compound 6 (25.8 g, 0.065 mol) was mixed with $PBu_3$ (13.2 g, 0.065 mol) in 200 ml of toluene. The mixture was refluxed for three days. After evaporating the solvent under vacuum, a glass-like Wittig salt (Compound 7) was obtained and used for the next reaction.

Example 2

Preparation of a Compound Having Formula IV

The following synthesis refers to representative compounds having Formula IV.
trans-[(N,N-di(2-ethanol)amino)phenylene-3-decanyl-2-thiophene]

To a solution of 3-decanyl-2-methyltributylphosphonium-thiophene bromide (26 g, 0.05 mol) and 4-[N,N-di-(2-hydroxyethyl)amino]benzaldehyde (12.6 g, 0.06 mol) in 200 ml of ethanol, $NaOC_2H_5$ (1 M in ethanol) was added dropwise. The resulting mixture was refluxed for 98 hours. After removal of this reaction from the oil bath, the solvent was evaporated, and the residue was extracted with ethyl ether (3×150 ml). The combined ether mixture was washed with water (100 ml), brine (2×100 ml) and dried over anhydrous $MgSO_4$. After removal of the solvent, the residue was purified by column chromatography on silica eluted using 50% ethyl acetate, 10% acetone, and 40% hexane to give the pure title compound with a yield of 16 g. Carbon and proton NMR were consistent with the structure.
trans-[(N,N-di(2-ethanol)amino)phenylene-2-thiene-3-decanyl-5-al]

To a 500 ml flask containing the compound synthesized above (10.44 g, 0.0243 mol), 200 ml of THF was added. The solution was cooled to −78° C. and n-BuLi (32 ml, 2.5 M in hexane) was added dropwise. The mixture was stirred for 2 hours followed by addition of DMF (6 ml). After warming to room temperature, the resulting solution was stirred overnight. After adding HCl (2 M, 50 ml) and stirring for an hour, the THF was evaporated. The residue was extracted with ethyl ether (3×100 ml). The combined organic solution was washed with saturated $Na_2CO_3$ solution (50 ml), water (100 ml), brine (100 ml) and dried over anhydrous $MgSO_4$. After evaporating the solvent, solid target compound (11.1 g, mp 107–109° C.) was obtained. HNMR showed that this is compound was pure enough for the next step.

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. A compound having Formula I

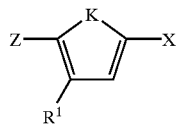

I wherein:

K is S;

Z is a chemical group capable of being linked to a donor;

$R^1$ is $—Q—C_nH_{2n+1}$, $—Q—(CH_2)_aC_nF_{2n+1}$, $—Q—CH_2OCH_2CF_3$, $—Q—CH_2SCH_2C_nF_{2n+1}$, or $—Q—CH_2SCH_2CF_3$; where n is 1–10 and a is 0–10, and Q is absent, O or S; and X is $(—CH=CH)_b—C(=O)H$; where b is 0–3.

2. The compound of claim 1 wherein a is 1–3, n is 1–3, and b is 0.

3. The compound of claim 2 wherein $R^1$ is $C_4–C_{10}$ or fluorine substituted $C_4–C_{10}$.

4. A compound having Formula I

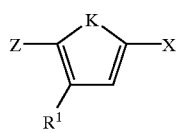

I wherein:

K is O or S;

Z is

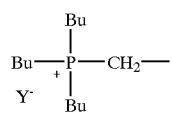

where $Y^-$ is $Br^-$, $I^-$, or $Cl^-$; p1 $R^1$ is $—Q—C_nH_{2n+1}$, $—Q—(CH_2)_aC_nF_{2n+1}$, $—Q—CH_2OCH_2CF_3$, $—Q—CH_2SCH_2C_nF_{2n+1}$, or $—Q—CH_2SCH_2CF_3$; where n is 1–10 and a is 0–10, and Q is absent, O or S; and X is H or $(—CH=CH)_b—C(=O)H$; where b is 0–3.

5. A compound having Formula III

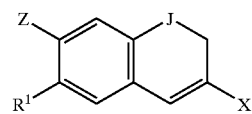

III wherein:

J is $CH_2$, O, or S;

Z is $—CH_2—Br$, $—CH_2—OH$, $—C(=O)H$, I, Br or

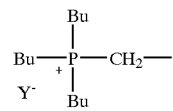

where $Y^-$ is $Br^-$, $I^-$, or $Cl^-$;

$R^1$ is $—Q—C_nH_{2n+1}$, $—Q—(CH_2)_aC_nF_{2n+1}$, $—Q—CH_2OCH_2CF_3$, $—Q—CH_2SCH_2C_nF_{2n+1}$, or $—Q—CH_2SCH_2CF_3$; where n is 1–10 and a is 0–10, and Q is absent, O or S; and X is $(C=O)H$ or $C=CH(—CH=CH)_d—C(=O)H$; where d is 0–3.

6. The compound of claim 5 wherein $R^1$ is $—Q—C_nH_{2n+1}$, $—Q—(CH_2)_aC_nF_{2n+1}$, $—Q—CH_2OCH_2CF_3$, $—Q—CH_2SCH_2C_nF_{2n+1}$, or $—Q—CH_2SCH_2CF_3$ and wherein a is 1–3, n is 1–3, and X is $(C=O)H$.

7. The compound of claim 6 wherein $R^1$ is $C_4–C_{10}$ or fluorine substituted $C_4–C_{10}$.

8. A compound having Formula IV

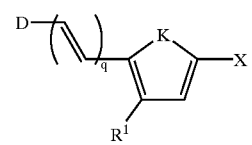

IV wherein:

D is an electron donating group;

K is O or S;

$R^1$ is $—Q—C_nH_{2n+1}$, $—Q—(CH_2)_aC_nF_{2n+1}$, $—Q—CH_2OCH_2CF_3$, $—Q—CH_2SCH_2C_nF_{2n+1}$, or $—Q—CH_2SCH_2CF_3$; where n is 1–10 and a is 0–10, and Q is absent, O or S;

q is 1, 2, or 3; and

X is H or $(—CH=CH)_b—C(=O)H$; where b is 0–3.

9. The compound of claim 8 having Formula VII

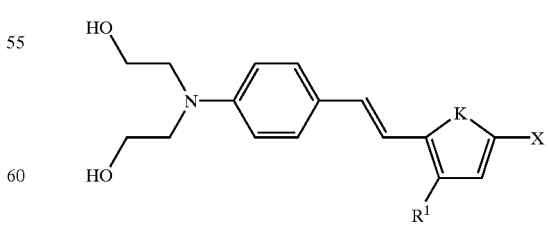

VII wherein:

K is O or S;

$R^1$ is $—Q—C_nH_{2n+1}$, $—Q—(CH_2)_aC_nF_{2n+1}$, $—Q—CH_2OCH_2CF_3$, $—Q—CH_2SCH_2C_nF_{2n+1}$, or

—Q—CH$_2$SCH$_2$CF$_3$; where n is 1–10 and a is 0–10, and Q is absent, O or S; and X is H or (—CH=CH)$_b$—C(=O)H; where b is 0–3.

10. The compound of claim 9 wherein R$^1$ is —Q—C$_n$H$_{2n+1}$, —Q—(CH$_2$)$_a$C$_n$F$_{2n+1}$, —Q—CH$_2$OCH$_2$CF$_3$, —Q—CH$_2$SCH$_2$C$_n$F$_{2n+1}$, or —Q—CH$_2$SCH$_2$CF$_3$ and wherein a is 1–3, n is 1–3, and b is 0.

11. The compound of claim 10 wherein R$^1$ is C$_4$–C$_{10}$ or fluorine substituted C$_4$–C$_{10}$.

12. A compound having Formula V

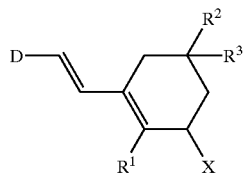

V wherein:

D is an electron donating group;

R$^1$ is —S—C$_n$H$_{2n+1}$, —O—C$_n$H$_{2n+1}$, —S—(CH$_2$)$_a$C$_n$F$_{2n+1}$, —O—(CH$_2$)$_a$C$_n$F$_{2n+1}$, —Q—CH$_2$OCH$_2$CF$_3$, —Q—CH$_2$SCH$_2$C$_n$F$_{2n+1}$, or —Q—CH$_2$SCH$_2$CF$_3$; where n is 1–10 and a is 0–10, and Q is absent, O or S; and X is (=O), or =CH(—CH=CH)$_d$—C(=O)H; and where d is 0–3; and R$^2$ and R$^3$ each, independently, are C$_1$, C$_2$ or C$_3$ alkyl.

13. The compound of claim 12 having Formula VIII

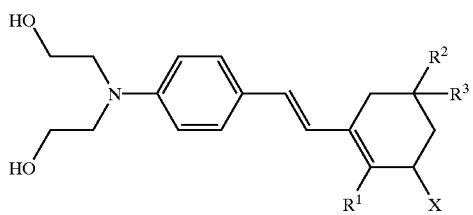

VIII wherein:

R$^1$ is —S—C$_n$H$_{2n+1}$, —O—C$_n$H$_{2n+1}$, —S—(CH$_2$)$_a$C$_n$F$_{2n+1}$, —O—(CH$_2$)$_a$C$_n$F$_{2n+1}$, —Q—CH$_2$OCH$_2$CF$_3$, —Q—CH$_2$SCH$_2$C$_n$F$_{2n+1}$, or —Q—CH$_2$SCH$_2$CF$_3$; where n is 1–10 and a is 0–10, and Q is absent, O or S; and X is (=O), or =CH(—CH=CH)$_d$—C(=O)H; and where d is 0–3; and R$^2$ and R$^3$ each, independently, are C$_1$, C$_2$ or C$_3$ alkyl.

14. The compound of claim 13 wherein R$^1$ is —S—C$_n$H$_{2n+1}$, —O—C$_n$H$_{2n+1}$, —S—(CH$_2$)$_a$C$_n$F$_{2n+1}$, —O—(CH$_2$)$_a$C$_n$F$_{2n+1}$, —Q—CH$_2$OCH$_2$CF$_3$, —Q—CH$_2$SCH$_2$C$_n$F$_{2n+1}$, or —Q—CH$_2$SCH$_2$CF$_3$ and wherein a is 1–3, n is 1–3, and X is (=O).

15. A compound having Formula VI

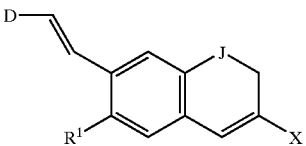

VI wherein:

D is an electron donating group;

J is CH$_2$, O or S;

R$^1$ is —Q—C$_n$H$_{2n+1}$, —Q—(CH$_2$)$_a$C$_n$F$_{2n+1}$, —Q—CH$_2$OCH$_2$CF$_3$, —Q—CH$_2$SCH$_2$C$_n$F$_{2+1}$, or —Q—CH$_2$SCH$_2$CF$_3$; where n is 1–10 and a is 0–10, and Q is absent, O or S; and X is (C=O)H, or C=CH(—CH=CH)$_d$—C(=O)H; where d is 0–10.

16. The compound of claim 15 having Formula IX

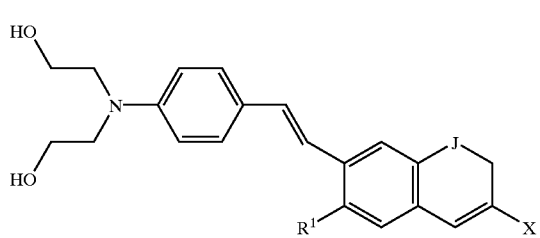

IX wherein:

R$^1$ is —Q—C$_n$H$_{2n+1}$, —Q—(CH$_2$)$_a$C$_n$F$_{2n+1}$, —Q—CH$_2$OCH$_2$CF$_3$, —Q—CH$_2$SCH$_2$C$_n$F$_{2n+1}$, or —Q—CH$_2$SCH$_2$CF$_3$; where n is 1–10 and a is 0–10, and Q is absent, O or S; and X is (C=O)H, or C=CH(—CH=CH)$_d$—C(=O)H; where d is 0–10.

17. The compound of claim 16 wherein R$^1$ is —Q—C$_n$H$_{2n+1}$, —Q—(CH$_2$)$_a$C$_n$F$_{2n+1}$, —Q—CH$_2$OCH$_2$CF$_3$, —Q—CH$_2$SCH$_2$C$_n$F$_{2n+1}$, or —Q—CH$_2$SCH$_2$CF$_3$ and wherein a is 1–3, n is 1–3, and X is (C=O)H.

18. The compound of claim 17 wherein R$^1$ is C$_4$–C$_{10}$ or fluorine substituted C$_4$–C$_{10}$.

19. A compound having Formula I:

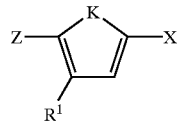

I wherein:

K is O or S;

Z is —CH$_2$—Br, —CH$_2$—OH, —C(=O)H, I, or Br;

R$^1$ is —Q—C$_n$H$_{2n+1}$, —Q—(CH$_2$)$_a$C$_n$F$_{2n+1}$, —Q—CH$_2$OCH$_2$CF$_3$, —Q—CH$_2$SCH$_2$C$_n$F$_{2n+1}$, or

—Q—CH$_2$SCH$_2$CF$_3$; where n is 1–10 and a is 0–10, and Q is absent, O or S; and X is (—CH=CH)$_b$—C(=O)H; where b is 0–3.

20. A compound having Formula I

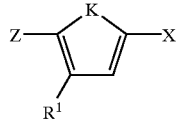

wherein:

K is O or S;

Z is a chemical group capable of being linked to a donor;

R$^1$ is —O—C$_n$H$_{2n+1}$, —S—C$_n$H$_{2n+1}$, —Q—(CH$_2$)$_a$C$_n$F$_{2n+1}$, —Q—CH$_2$OCH$_2$CF$_3$, —Q—CH$_2$SCH$_2$C$_n$F$_{2n+1}$, or —Q—CH$_2$SCH$_2$CF$_3$; where n is 1–10 and a is 0–10, and Q is absent, O or S; and X is (—CH=CH)$_b$—C(=O)H; where b is 0–3.

21. A compound having Formula I

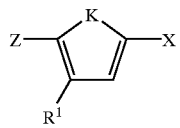

wherein:

K is C or S;

Z is a chemical group capable of being linked to a donor;

R$^1$ is —Q—C$_n$H$_{2n+1}$, —Q—(CH$_2$)$_a$C$_n$F$_{2n+1}$, —Q—CH$_2$OCH$_2$CF$_3$, —Q—CH$_2$SCH$_2$C$_n$F$_{2n+1}$, or —Q—CH$_2$SCH$_2$CF$_3$; where n is 1–10 and a is 0–10, and Q is absent, O or S; and X is (—CH=CH)$_b$—C(=O)H; where b is 1–3.

22. A compound having Formula III

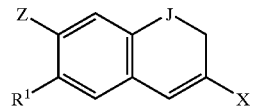

wherein:

J is O or S;

Z is a chemical group capable of being linked to a donor;

R$^1$ is —Q—C$_n$H$_{2n+1}$, —Q—(CH$_2$)$_a$C$_n$F$_{2n+1}$, —Q—CH$_2$OCH$_2$CF$_3$, —Q—CH$_2$SCH$_2$C$_n$F$_{2n+1}$, or —Q—CH$_2$SCH$_2$CF$_3$; where n is 1–10 and a is 0–10, and Q is absent, O or S; and X is (C=O)H or C=CH(—CH=CH)$_d$—C(=O)H; where d is 0–3.

23. A compound having Formula III

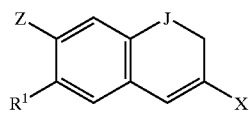

wherein:

J is CH$_2$, O, or S;

Z is a chemical group capable of being linked to a donor;

R$^1$ is —C$_n$H$_{2n+1}$, —S—C$_n$H$_{2n+1}$, —Q—(CH$_2$)$_a$C$_n$F$_{2n+1}$, —Q—CH$_2$OCH$_2$CF$_3$, —Q—CH$_2$SCH$_2$C$_n$F$_{2n+1}$, or —Q—CH$_2$SCH$_2$CF$_3$; where n is 1–10 and a is 0–10, and Q is absent, O or S; and X is (C=O)H or C=CH(—CH=CH)$_d$—C(=O)H; where d is 0–3.

24. A compound having Formula III

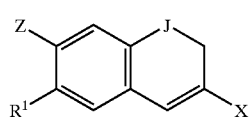

wherein:

J is CH$_2$, O, or S;

Z is a chemical group capable of being linked to a donor;

R$^1$ is —Q—C$_n$H$_{2n+1}$, —Q—(CH$_2$)$_a$C$_n$F$_{2n+1}$, —Q—CH$_2$OCH$_2$CF$_3$, —Q—CH$_2$SCH$_2$C$_n$F$_{2n+1}$, or —Q—CH$_2$SCH$_2$CF$_3$; where n is 1–10 and a is 0–10, and Q is absent, O or S; and X is C=CH(—CH=CH)$_d$—C(=O)H; where d is 0–3.

* * * * *

UNITED STATES PATENT AND TRADEMARK OFFICE
CERTIFICATE OF CORRECTION

PATENT NO. : 6,514,434 B1
DATED : February 4, 2003
INVENTOR(S) : Mingqian He and Thomas M. Leslie It is certified that error appears in the above-identified patent and that said Letters Patent is hereby corrected as shown below:

<u>Column 11,</u>
Line 61, delete "p1" before "$R^1$"

<u>Column 15,</u>
Line 34, "C" should be -- O --

Signed and Sealed this

Tenth Day of June, 2003

JAMES E. ROGAN
*Director of the United States Patent and Trademark Office*